US008571177B2

(12) United States Patent
Thorne et al.

(10) Patent No.: US 8,571,177 B2
(45) Date of Patent: Oct. 29, 2013

(54) GONIOMETER BASE APPARATUS AND METHOD (75) Inventors: Robert E. Thorne, Ithaca, NY (US); Benjamin Apker, Barton, NY (US); Eric Hunt, Interlaken, NY (US)

(73) Assignee: Cornell University, Ithaca, NY (US)

( * ) Notice: Subject to any disclaimer, the term of this patent is extended or adjusted under 35 U.S.C. 154(b) by 280 days.

(21) Appl. No.: 13/037,715

(22) Filed: Mar. 1, 2011

(65) Prior Publication Data
US 2011/0211674 A1 Sep. 1, 2011

Related U.S. Application Data (60) Provisional application No. 61/309,048, filed on Mar. 1, 2010.

(51) Int. Cl.
*G01N 23/207* (2006.01)
(52) U.S. Cl.
USPC ................................................ 378/73; 378/81

(58) Field of Classification Search
USPC ........................................ 378/68, 73, 79, 81
See application file for complete search history.

(56) References Cited

U.S. PATENT DOCUMENTS

| 4,644,761 | A  | * | 2/1987  | Chatzipetros et al. | ......... 62/51.1 |
|-----------|----|---|---------|---------------------|------------------|
| 6,404,849 | B1 | * | 6/2002  | Olson et al.        | ........ 378/79   |
| 7,274,769 | B2 | * | 9/2007  | Nordmeyer et al.    | ......... 378/80  |
| 7,438,472 | B1 | * | 10/2008 | Lazarski et al.     | ........ 378/205  |
| 7,542,546 | B2 | * | 6/2009  | Thorne et al.       | ........ 378/79   |
| 2007/0228049 | A1 | * | 10/2007 | Nordmeyer et al. | ..... 220/560.07 |

* cited by examiner

*Primary Examiner* — Irakli Kiknadze
(74) *Attorney, Agent, or Firm* — William Greener; Bond, Schoeneck & King, PLLC (57) ABSTRACT A goniometer base for X-ray crystallography comprises a magnetic steel part with a cylindrical hole, a compliant cylindrical part that is inserted into this hole, and a cylindrical tube that is press-fit into the hole and holds the compliant part in place, such that when a crystal mounting tool is inserted through the concentric holes in each part, it is positively gripped and held in place at both T=300 K and T=100 K.

24 Claims, 4 Drawing Sheets

GONIOMETER BASE APPARATUS AND METHOD

RELATED APPLICATION

The present application claims priority to U.S. provisional patent application No. 61/309,048, filed on Mar. 1, 2010; all of the foregoing patent-related document(s) are hereby incorporated by reference herein in their respective entirety(ies).

FEDERALLY SPONSORED RESEARCH OR DEVELOPMENT

This invention was made with partial government support under a Phase I STTR Grant to Mitegen, LLC, Grant No. R41 TM075361-01 A1 awarded by the National Institutes of Health. The government has certain rights in the invention.

BACKGROUND OF THE INVENTION

1. Field of the Invention

The present invention relates to systems for irradiating samples at cryogenic temperatures, more particularly to X-ray crystallography systems, and even more particularly to goniometer bases used in X-ray crystallography systems.

2. Description of the Related Art

X-ray crystallography is a primary method for determining the molecular structure of inorganic compounds, organic compounds (including those of pharmaceutical relevance), proteins, nucleic acids and viruses. In this method, a sample (usually a crystal) to be examined is held in an X-ray beam, and the X-rays diffracted by the sample are measured using a detector. The sample orientation is changed in a precisely controlled manner, usually by rotating it about one or more axes using a motor-driven goniometer stage, and diffraction data is collected at multiple orientations. These data from different orientations are then merged and analyzed to determine the molecular structure. Because most crystals are easily damaged by the X-ray beams, X-ray data is typically collected on frozen samples, with a cold (T=100 K) gas stream flowing over the sample during measurements. Herein, the term "cryogenic temperatures" will be used to mean temperatures below T=180 K, low enough to perform X-ray crystallography without excessive sample damage due to X-rays. It is noted that the sample studied in X-ray "crystallography" does not always necessarily have a crystal structure.

Most small molecule and protein/biomolecule crystallography is now performed using a standard set of tools. A crystal is retrieved using a tool (hereinafter, "crystal holding tool") consisting of an X-ray transparent loop or tip attached to a small (typically 0.64 mm (0.025 inch) diameter, 19 mm long) steel rod (hereinafter, "crystal holding tool rod" or "rod"). These crystal mounting tools are currently sold under trade names such as CryoLoop (Hampton Research, Aliso Viejo, Calif.), MicroMount and MicroLoop (MiTeGen, LLC, Ithaca, N.Y.), and LithoLoop (Molecular Dimensions). (Note: the terms "CryoLoop," "MicroMount," "LithoLoop" and/or "MicroLoop" may be subject to trademark rights in various jurisdictions throughout the world and are used here only in reference to such trademarked products or services to the extent that such trademark rights may exist.)

The rods of these tools are inserted into goniometer bases (hereinafter referred to as "goniometer bases" or "bases") or "caps" (so-called because the first bases were derived from the caps of cryogenic vials), and then glued into the bases using epoxy or other adhesive to firmly secure them. In other words, the rod receiving hardware set in these conventional goniometer bases is made up of some type of recess for receiving the rod and epoxy for rigidly mechanically connecting to the goniometer base. This rigid connection formed by the hardened epoxy prevents the rod from moving with respect to the goniometer base. Conventionally, it is believed that this rigid connection is a desirable feature because it prevents the rod from moving around, relative to the precisely controlled goniometer stage and to the X-ray beam, when the rod assembly and the sample it holds are subjected to cryogenic gas flows and/or cryogenic fluid flows. This rigid connection is also a desirable feature to prevent the rod from moving relative to the base, including falling out of the goniometer base, due to forces during goniometer rotation and in other routine handling.

These bases are then attached to the rotating goniometer stage assembly. The goniometer stage assembly generally contains a magnet-containing goniometer head that holds and orients the goniometer base, which holds and orients the crystal holding tool rod and rod-receiving hardware set, which holds and orients the sample in the X-ray beam at a precisely controlled position and angular orientation in three-space.

Figure 1A:
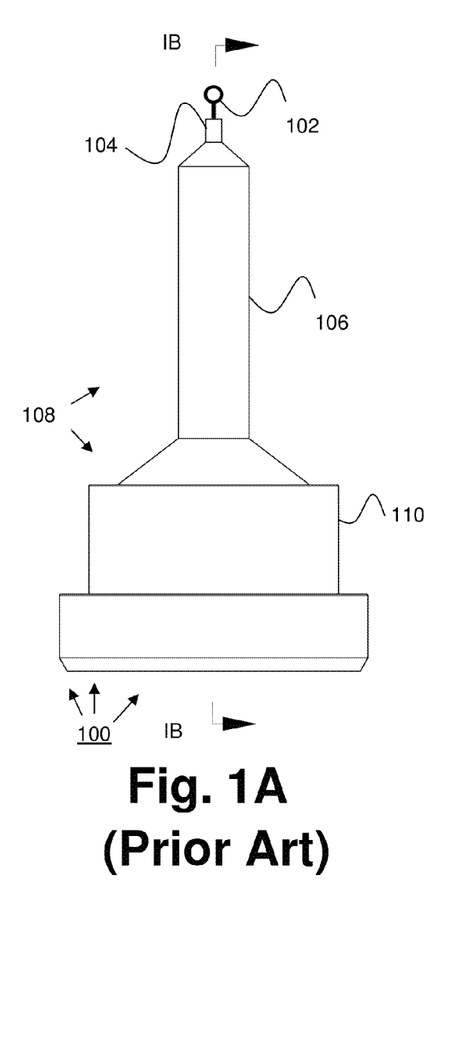
FIG. 1A, 1B, respectively, shows a schematic plan view and a schematic cross sectional view of a current commercially available goniometer base. The plan view shows a Cryoloop (nylon loop attached to a hollow stainless steel rod) crystal holding tool inserted.
Figure 1B:
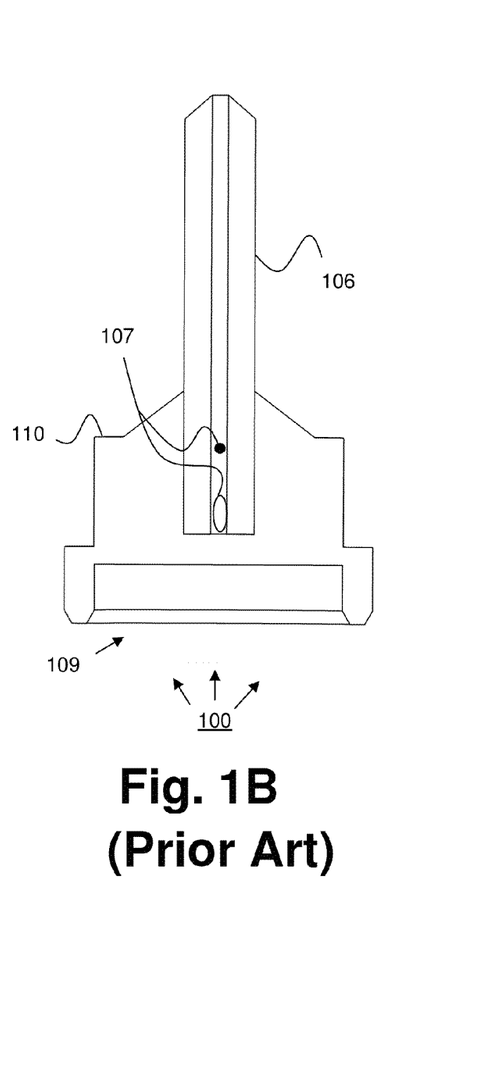
Figure 2A:
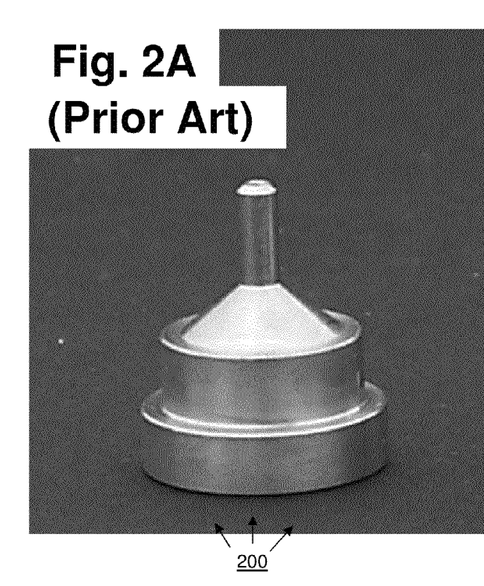
FIGS. 2A to 2E show commercially available goniometer bases.

FIG. 1A shows goniometer base and crystal holding tool assembly 100 including: sample holding loop 102; rod 104; and goniometer base housing 108. Housing 108 encloses a rod receiving hardware set (not shown, generally including a rod recess and epoxy) and a stage connection hardware set (not shown, for mechanically connecting the goniometer base to the goniometer stage assembly) In one tool set that is particularly well-suited to high-throughput automated sample handling, housing 108 consists of two parts: a magnetic stainless steel base member 110 and a copper upper part 106, as shown in FIG. 1A, FIG. 2C (goniometer base 220), and FIG. 2D (goniometer base 230). It is copper upper part 106 that contains the rod receiving hardware set 107, which is basically made up of epoxy and a hole, as shown in FIG. 1B. In other goniometer base assemblies the base includes only a single magnetic stainless steel part, as shown in FIG. 2A (goniometer base 200) and FIG. 2B (goniometer base 210), that contains the rod receiving hardware set and also any necessary hardware for attaching to the goniometer stage assembly. The bottom of the base is secured to a magnet-containing goniometer head (not shown) that rotates and translates to position the sample in the X-ray beam. In the other common tool set (used almost exclusively in small molecule crystallography), a single piece brass or stainless steel base 240 as shown in FIG. 2E is held in a hole in the goniometer head using a set screw. Goniometer bases 200, 210, 220, 230 (respectively shown in FIGS. 2A-2D) are for use with magnetic goniometer heads. Herein, goniometer bases for use with magnetic goniometers will be specifically referred to as magnetic goniometer bases.

There are several shortcomings with the current technology, in use for nearly 20 years, recognized by those skilled in the art. All current commercial goniometer bases simply have cylindrical holes into which the crystal holding tool rod is inserted, thus the bases do not positively grip the rods to keep the crystal holding tool rod from falling out of the base during handling (which can cause automated handlers to fail). The conventional thinking is that this problem is best overcome by gluing the rod into the base, most commonly using an epoxy.

Because of the sub-millimeter dimensions of the crystal holding tool rod, this gluing of rods into bases is difficult and time consuming, especially in the quantities of hundreds to thousands required in modern high-throughput crystallography. The vertical positioning of the crystal holding tool in the base (i.e., the distance between the bottom of the base and the crystal-holding aperture) is fixed once the glue sets and cannot later be adjusted to optimize the crystal's position in the X-ray beam. When the tip 102 of the crystal holding tool becomes damaged (a common occurrence), both the crystal holding tool and base are typically discarded, rather than incurring the time and expense involved in removing the old glue and regluing.

Nylon loop crystal holding tools (CryoLoops) are rapidly being replaced with higher performance but more fragile microfabricated polymer film tools, which must be periodically replaced.

However, the above-noted drawbacks of rigid connections between goniometer bases, and the rods that they hold, are currently generally considered as acceptable because of the degree of securement and positional stability provided to the rod.

BRIEF SUMMARY OF THE INVENTION

The present invention recognizes that there is a need for goniometer bases that reduce the effort and cost required in initially assembling a base and crystal holding tool and in replacing the crystal holding tool. The present invention recognizes that more efficient automated alignment of the crystal in the X-ray beam could be achieved if the position of the crystal aperture in the crystal holding tool relative to the bottom of the goniometer base could be made more precise and reproducible. Achieving this precision when the tools are glued into the base is not easy and requires specialized apparatus to hold the crystal holding tool in place while the glue sets. The present invention recognizes that there is a need for a goniometer base that simplifies precision assembly of the crystal holding tool into the base.

Before moving to some of the currently-preferred aspects of the present invention, first some currently-less-preferred embodiments will be mentioned in passing to help give an idea of the broad potential scope of the present invention. Within the broad potential scope of the present invention, a variety of approaches can, in principle, be used to achieve positive capture without the need for gluing. However, the small diameter of the crystal holding tool rods (typically 0.64 mm) and of the goniometer bases (which are constrained by high-density storage requirements and by the desire to minimally perturb the cold gas streams that flow over the sample during data collection) make challenging the implementation of a positive grip action in an inexpensive way. The potential scope of the present invention may include various types of rod receiving hardware that include devices such as chucks, set screws, and tapered compression (as in pin vises and mechanical pencils). Collectively, these possibilities will be called "mechanical design rod receiving hardware sets." However, these embodiments would require small, difficult-to-manufacture and assemble parts that, because of the requirement of cryogenic compatibility, would be costly to produce in the relatively small quantities generally required in this application. Also, once the rod is fully engaged with the rod receiving hardware (for example, the tiny chuck), it would no longer be possible for a user to adjust the rod along its axial direction because the chuck would prevent such movement. Although rod receiving hardware, such as a tiny chuck, could be disengaged in order to allow for axial adjustment according to the present invention, this could be burdensome for the user, especially in view of the small size and delicacy of mechanical design rod receiving hardware sets.

O-rings represent another currently-not-preferred embodiment which may be within the broad scope of the present invention because they can allow for axial adjustability of the rod relative to the base. However, because of the small gripping surface area, the amount of deformation and/or compression required to get adequately strong gripping at both room temperature (at which crystals are mounted) and at T=77-100 K (when they are stored, transported, and held in the X-ray beam) is large. As a result, temperature cycling in routine use may cause o-ring cracking and failure. Again, because of the small gripping surface area and small cross-section of o-rings, any chips or cracks in the o-ring can lead to a complete failure of gripping. On the other hand, unlike the mechanical design rod receiving hardware sets, o-ring-based rod receiving hardware sets may (depending upon the structure of the o-ring and the surface(s) that frictionally engage the o-ring) allow the user to adjust the position of the rod in its axial position, even when the rod is engaged by the friction fit of the o-ring. In other words, at least some o-ring embodiments may simultaneously: (i) reliably secure the rod against forces typically encountered under normal operating conditions, and (ii) still allow the user to freely adjust the axial position of the engaged rod by pushing or pulling against the friction fit.

Discussion will now move to the currently-preferred aspects of the present invention. The currently-preferred embodiment of the present invention includes a rod receiving hardware set with a resilient insert having a recess (for example, a cylindrical hole) sized to form a force fit with the rod. These resilient insert embodiments simultaneously: (i) reliably secure the rod as against forces typically encountered under the range of normal operating conditions experienced during X-ray crystallography, and (ii) still allow the user to freely adjust the axial position of the engaged rod by pushing against the force fit of the resilient insert. The use of an insert is conducive to a goniometer base mainly made of materials with suitable magnetic and/or thermal properties for X-ray crystallography, such as stainless steel and copper. The use of a resilient insert is conducive to one part goniometer base housing designs as well as multiple part goniometer base housing designs. Some embodiments of the present invention have perfect cylindrical symmetry which can be helpful for at least certain kinds of X-ray crystallography.

BRIEF DESCRIPTION OF THE DRAWINGS

The present invention will be more fully understood and appreciated by reading the following Detailed Description in conjunction with the accompanying drawings, in which.

DETAILED DESCRIPTION OF THE INVENTION

Figure 3A:
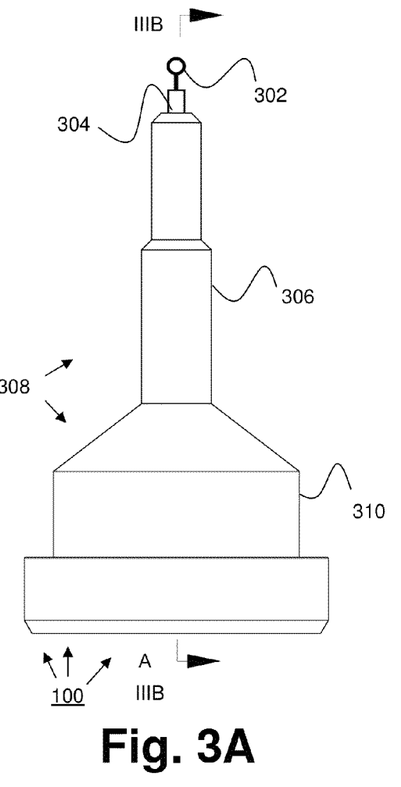
FIGS. 3A and 3B, respectively, show a schematic plan view and a schematic cross sectional view of a first embodiment of a goniometer base according to the present invention (the plan view shows a Cryoloop (nylon loop attached to a hollow stainless steel rod) crystal holding tool inserted and cross-hatching has been omitted in FIG. 3B for clarity of illustration)
Figure 3B:
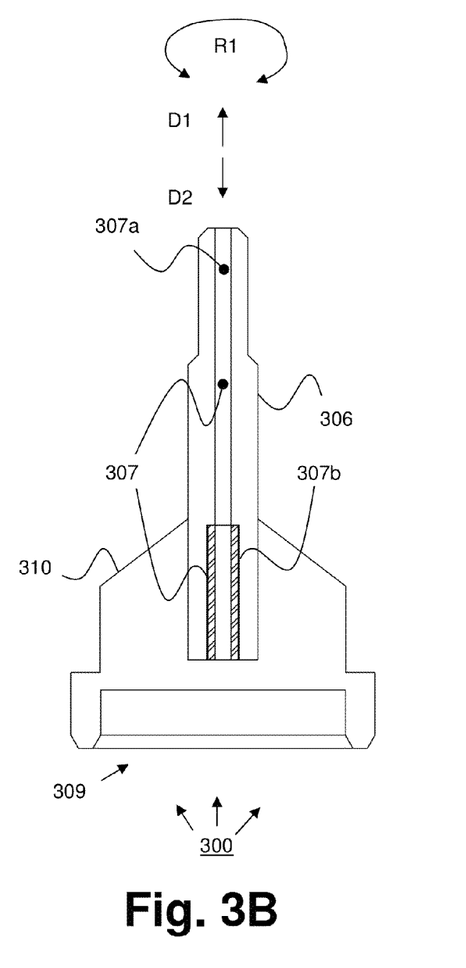

FIGS. 3A and 3B show goniometer base system 300 including: sample holding loop 302; rod 304; rod receiving hardware set 307 (including recess 307a and resilient insert 307b) goniometer base housing 308 (including upper portion 306 and lower portion 310); and stage engaging hardware set 309. System 300 is directed to a goniometer base for X-ray crystallography that can positively hold a crystal holding tool rod in a manner that allows the rod to be adjusted axially and rotationally (with respect to the cylindrical co-ordinate system defined by the rod and/or recess 307a) and to be replaced, that is compatible with cryogenic temperatures between 4 K and 180 K, and that can withstand repeated temperature cycling between room temperature and cryogenic temperature without damage or loss of positive hold. The embodied structure eliminates the need for gluing and allows easier and more precise assembly of the crystal holding tool in the base.

Resilient insert 307b is disposed coaxially with the base and with the crystal holding tool rod 304.

A non-limiting illustrative embodiment of the invention is shown in FIG. 3. The goniometer base housing includes two metal parts 306,310 that are disposed with cylindrical symmetry. They can be manufactured by, e.g., screw machine shops. The lower portion 310 is of a material such as 416 stainless steel that is strongly attracted to a magnet. This part detachably attaches to a magnet-containing goniometer head through stage engagement hardware set 309. The upper portion 306 is typically made of copper to provide high thermal conductivity and uniform temperature along its length, but may be made be of any suitable metal or plastic (or any other suitable material now known or to be developed in the future). This part helps to reduce formation of ice along the rod of the crystal holding tool when it is inserted in a cold gas stream. The upper and lower parts are threaded, and the upper portion screws into the lower portion. The housing 308 contains rod receiving hardware set 307. Rod receiving hardware set 307 includes aperture (or central hole) 307a that receives at crystal holding tool rod 304. This central hole is sized and shaped so that: (i) rod 304 is closely constrained in the radial direction; but (ii) the rod can freely move with respect to the aperture in its axial (see FIG. 3B at reference numerals D1 and D2) and angular (see FIG. 3B at reference numeral R1) directions.

To obtain a reusable base, the upper portion 306 is modified to have a larger-diameter cylindrical cavity its lower half in order to accommodate resilient insert 307b. Insert 307b includes a rod receiving recess (no separate reference numeral) to accept the lower axial portion of rod 304 by a resilient force fit. The force fit: (i) is sufficiently loose so the rod can be freely adjusted in the axial direction by a user (by hand and or by a tool); but (ii) sufficiently tight so that the rod does not move, relative to the base and the insert, during normal x-ray crystallography operations (including normal temperature cycling, gas currents and/or fluid currents). The dimensioning and tolerancing will depend on the material properties of the materials used for the insert and on the dimensioning and/or tolerancing of the rod. Insert 307b is cylindrical and compliant. While the insert in this embodiment is unitarily formed of a single piece, this is not necessarily required. While the insert in this embodiment is cylindrically shaped, and has a recess in the form of a cylindrical through hole (which through hole is coaxial with the outer surface of the insert), this is not necessarily required. For example, the outer surface of the insert may be shaped to prevent relative rotation of between the insert and the rest of the goniometer base. As a further example, the rod and recess may be shaped to prevent relative rotation between the rod and the recess in the insert (for example, they may be shaped as corresponding polygonal prism surfaces).

The insert 307b has a partial or full (through) aperture that can receive an end of the rod 304 and hold it securely in place via a friction-type fit. This will allow the rod to be rotated (in direction R1) and moved up and down axially (in directions D1 and D2) to optimize the position of the tool's loop or aperture relative to the X-ray beam. It also allows the rod to be removed entirely and replaced, eliminating the need for gluing and allowing the base to be reused.

Insert 307b can be made of a variety of compliant and resilient materials including natural or synthetic rubber, neoprene, silicone and Teflon, or similar material(s). These materials are mechanically tough and wear resistant and have good elasticity. Moreover, their thermal contraction and elasticity are such that they retain their gripping strength and ability to hold a crystal holding tool rod at cryogenic temperatures. They can also withstand being cooled (and warmed) hundreds of times between about 295 K and 77 K in normal use without failure of hold.

In an aspect, the central hole diameter of the recess in insert 307b is made slightly smaller than the diameter (0.63 mm) of the crystal holding tool rod 340 to provide a secure but adjustable friction-type fit. Suitable insert materials are available from, e.g., National Rubber Company, and are typically made by extrusion. In one implementation, the insert is neoprene rubber and has an outer diameter of 0.048 inches (1.22 mm) and an inner diameter of 0.02 inches (0.51 mm.).

The length of the insert 307b can vary over a significant range but is generally about 5 mm. This gives a much longer gripping length and much larger gripping area compared to an o-ring, and thus reduces the gripping pressure required to achieve a given gripping force on the rod 304. In some embodiments (herein called long insert embodiments) the axial length of the recess will be greater than the radial dimension length (for example, the inner diameter in cylindrical embodiments) of the recess. In other embodiments (herein called o-ring embodiments), the axial length of the inner recess will be smaller than the inner radial dimension length of the recess. Long insert embodiments may be preferred because smaller pressures mean less wear of the insert material when the rods are inserted and removed, and also less chance of damage to the insert. A long gripping length ensures continued strong gripping even if a portion of the insert becomes damaged.

Insert 307b need not be under compression to provide good holding force, and so the outer diameter of the insert can match to or be made slightly smaller than the inside diameter of the cavity into which it is inserted, for easy assembly.

The gentle pressure exerted by the insert on the rod allows the rod to be rotated and moved up and down axially to optimize the position of the tool's loop, and the sample it holds, relative to the X-ray beam. It also allows the rod to be removed entirely and replaced. This eliminates the need for time consuming gluing, and eliminates the issue of rods falling out due to glue failure (for example, after when the glue fails due to repeated temperature cycling). The present invention allows rods and bases to be used in an interchangeable manner so that: (i) each rod can be used, over time, with many different bases; and (ii) each base can be used, over time, with many different rods.

Figures 4, 5:
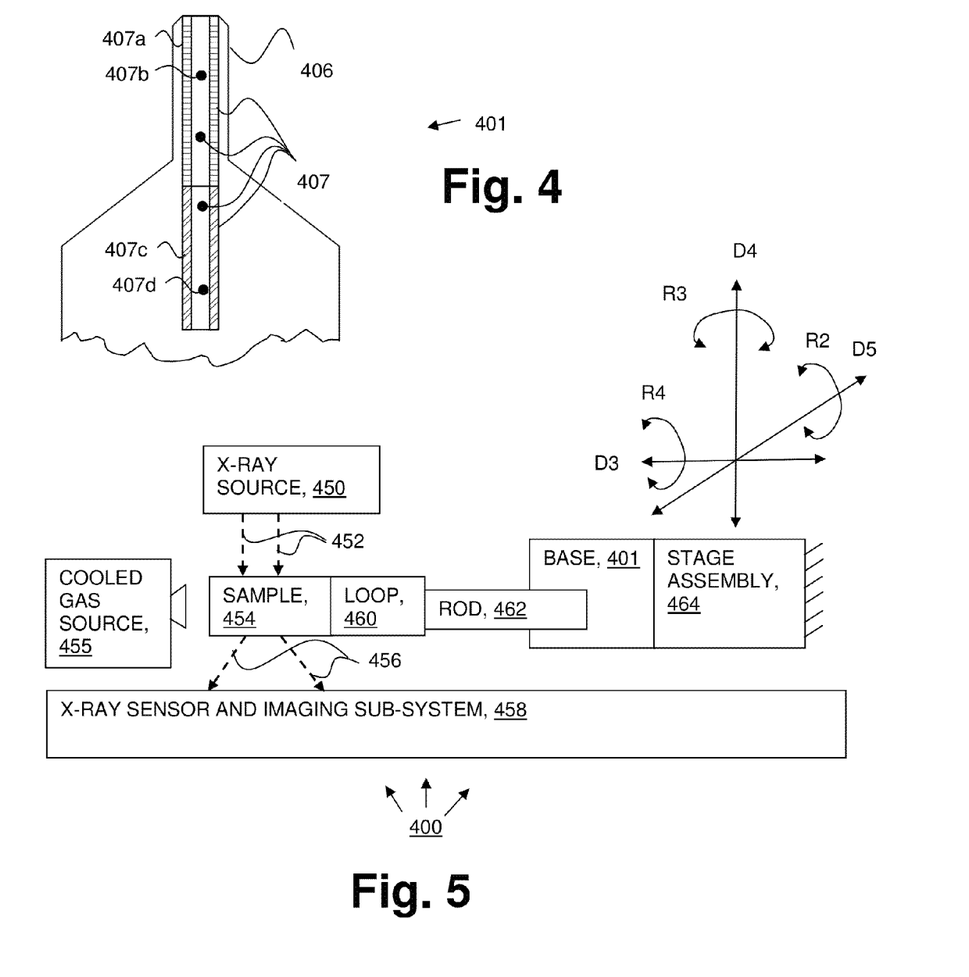
FIG. 4 shows an orthographic, front, cross-sectional view of a portion of a goniometer base according to a second embodiment of the present invention (cross-hatching omitted for clarity of illustration)
FIG. 5 shows a schematic view of a first embodiment of an X-ray crystallography system according to the present invention, which system includes the second embodiment goniometer base.

FIGS. 4 and 5 show an x-ray crystallography system 400 including: goniometer base 401; x-ray source 450; undiffracted x-rays 452; cooled gas source 455; sample 454; diffracted x-rays 456; x-ray sensor and imaging sub-system 458; loop 460; rod 462; and stage assembly 464. Base 401 includes: upper housing portion 406; and rod receiving hardware set 407. Rod receiving hardware set 407 includes: tube 407a; tube aperture 407b; insert 407c; and insert aperture 407d. It is noted that stage assembly 464 would include a magnetic goniometer head. It is further noted that, as with currently-conventional goniometer stages, the stage assembly 464 may be positionally adjustable with multiple degrees of freedom. For example, stage 464 may be positionally adjustable in rotational directions R2,R3,R4 (respectively about orthogonal axes D3,D4,D5). Cooled gas source 455 discharges cryogenically cooled gas in the vicinity of sample 454 in order to cool the sample down to a temperature suitable for X-ray crystallography.

Figure 2B:
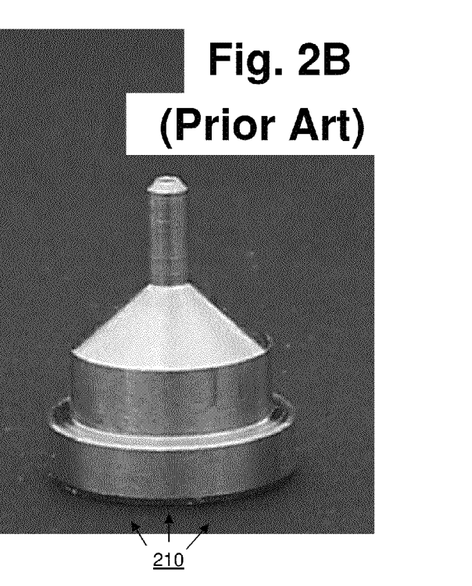
Figure 2C:
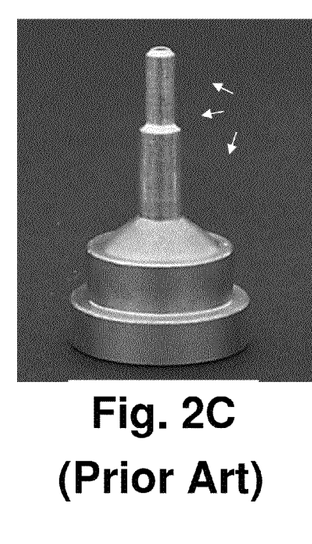
Figures 2D, 2E:
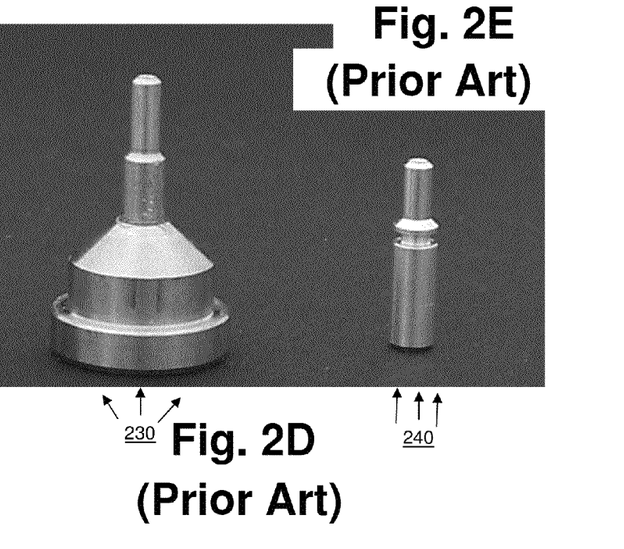

Base 401 may be used to replace prior art goniometer bases 200 and 210 (see FIGS. 2A and 2B). Housing 406 is made of magnetic stainless steel and attaches to the goniometer head (not shown, part of stage assembly 464). The diameter of a central aperture in the upper housing part is sufficiently large to accept: (i) a compliant and resilient insert 407c that is disposed coaxially with the base; and (ii) tube 407a. Aligned apertures 407b,407d in the tube and insert accept the end of crystal holding tool rod 462. The compliant insert 407c has a partial or full central aperture that is slightly smaller than the diameter of the crystal holding tool rod 462 and of the central aperture 407b in the tube 407a. The insert is held in place by metal or plastic cylindrical tube 407a. This tube may be press-fit or glued into the aperture in the goniometer base. As explained above in connection with insert 307b, insert 407c likewise grips and holds the rod by a friction type fit. This same approach can be used to make a positive gripping version of the goniometer base 240 shown in FIG. 2E (used in small molecule crystallography).

In use with resilient insert containing bases according to the present invention, such as base 300 or base 401, the rod of the crystal holding tool is inserted into the central aperture defined in the base (for example, by the housing, by a tube) and pushed down into the resilient insert, where the insert grabs and holds it by a friction-type fit. The holding force can be adjusted by adjusting the diameter of the central aperture in the compliant insert, by changing the length of the insert, by making the insert diameter slightly larger than the aperture in part, or by cutting the insert to be somewhat longer than the axial length of the interior space in the goniometer base that accommodates the insert (so that the resilient insert will be axially compressed when in position inside of the goniometer base housing), With respect to this last point about making the insert a bit longer than the axial length of the interior space that accommodates the resilient insert, this can be accomplished in at least a couple of different ways as will now be discussed. As shown in FIG. 3B, in embodiment 300, the upper portion 306 screws into lower portion 310 to form housing 308 and to define the interior space that holds resilient insert 307b. In this kind of embodiment, insert 307b can be made slightly longer than the axial length of the aperture in upper portion 306 that accommodates the insert. When assembling the base: (i) the resilient insert is inserted into the upper portion; and then (ii) the sub-assembly including the upper portion and the insert is screwed into the lower portion to form the base with an axially-compressed resilient insert. On the other hand, embodiment 401 (see FIG. 4) has a single piece housing. This is why: (i) resilient insert 407c must be inserted through the aperture at the top of upper portion 406 of the single piece housing; (ii) the aperture in the single piece housing is made wide enough to accept the resilient insert; and (iii) tube 407a is placed over the resilient insert to secure it in place in the axial direction. In this type of embodiment, it is the length of the tube that will effectively define the axial length of the interior space for the resilient insert. By making the tube longer, the resilient insert will be more compressed in its axial direction.

While a couple of embodiments of the present invention have been discussed in detail, it should be recognized that one feature common to some embodiments of the present invention is the feature of a releasable (or detachable) engagement between the rod and the rod receiving hardware set. When the rod is engaged with the rod receiving hardware set, it will not move axially under normal operating conditions, but the rod may be disengaged from the rod receiving hardware set so that it can be released from the goniometer base without damage to the rod and/or the components of the base. A further feature that is common to some embodiments of the present invention (including base 300 and base 401) is that the axial position of the rod, relative to the base, is freely adjustable by a user even when the rod is engaged with the rod receiving hardware. This axial position adjustability in the engaged position is the result of designing the holding force to be small enough that the rod can be rotated, moved axially, and removed and replaced. However, there may also be embodiments of the present invention where the rod cannot be adjusted axially without first disengaging the rod and rod receiving hardware. For example, if the rod receiving hardware is mainly constituted by a tiny chuck, then the rod would be removable, and it would also be axially adjustable, but the chuck would need to be disengage to either release the rod or to merely adjust its axial position. This is different than the resilient insert embodiments of the present invention where the rod remains engaged with the insert, even though a user can deliberately adjust the axial position of the engaged rod.

Tests on prototypes using neoprene rubber inserts have shown that gripping strength is largely undiminished after 100 cycles between T=300 K and T=100 K, and after 100 insertions and removals of the rods of standard crystal mounting tools.

In an alternative embodiment, the cylindrical insert was formed as a solid cylinder of a compliant and resilient material such as natural or synthetic rubber, which was inserted into the cavity in the lower surface of upper portion 306 of FIG. 3B, replacing insert 307b. The diameter of this cylinder should be comparable to the diameter of this cavity so that the interior space in the goniometer housing effectively secures the location of the insert in the radial direction. A crystal holding tool rod 304 inserted into the aperture at the top of upper portion 306 can then be pushed down into this insert, piercing it and become gripped by it with an intermediate gripping force so that: (i) the rod will not move axially under normal operational stresses and strains; but (ii) the axial position of the rod is freely adjustable by a user.

In a modification of embodiment 300, lower portion 310 (shown in FIG. 3B) could be formed with a cylindrical protrusion of diameter slightly smaller than the diameter of the cavity in the lower surface of upper portion 306 that holds compliant insert 307b. Under this modification, when the upper and lower portions of the goniometer base housing are screwed together to form housing 308, this protrusion would compress the insert and increase its gripping action. A washer may be added between the insert and the protrusion to make it easier for the insert to compress without twisting as the goniometer base housing is screwed shut.

In another alternative embodiment, the compliant and elastic insert could be replaced with a soft, plastically deformable material like putty or grease or a viscoelastic material such as a viscoelastic polymer, which could be inserted or injected in place prior to assembly. Again in this type of embodiment: (i) the rod would be releasably engaged with the base; (ii) the rod would not move axially under normal operating conditions when engaged with the base; and (iii) a user could freely adjust the axial position of the rod with respect to the base.

In other alternative embodiments of the present invention, the insert may move axially with respect to the goniometer base through a bounded range of motion. In these embodiments the rod is pushed in the axial direction to engage with the insert. This engagement is preferably by a force fit between the exterior surface of the rod and a resilient recess in the insert body, but it could be engagement by other mechanical design techniques, like chucking. Once the rod is engaged with the insert, pushing or pulling on the rod, in the axial direction, will cause the rod and insert to move as a single assembly with respect to the goniometer base. Preferably, in these embodiments, a resilient outer surface of the insert frictionally engages with a corresponding interior surface within the goniometer base. These surfaces may be cylindrical to allow for relative rotation between the base and insert, or they may be shaped to prevent relative rotation (for example, shaped as corresponding polygonal prisms). Preferably in these embodiments there would be stopping surfaces to limit the range of axial direction motion of the insert in the inwards and outwards directions. In these embodiments, the insert may further be structured with user actuation hardware (such as a handle attached to the insert and extending out of the base) so that a user can move the insert/rod assembly in the axial direction without pushing or pulling on the rod (which might be delicate) by transmitting force through the user actuation hardware instead. Some non-limiting exemplary embodiments and aspects of the invention include the following:

Example 1

A reusable goniometer base for use in protein and small molecule X-ray crystallography at cryogenic temperatures, comprising a cylindrical lower part of magnetic stainless steel, having a solid continuous bottom that attaches to a magnet containing goniometer head, and a hole threaded into its top for capturing the upper part; a cylindrical upper part having a threaded outer diameter at its bottom that screws into the threaded hole of the lower part, further comprising a central hole of diameter 0.028-0.035" into which a tool for holding a crystal is inserted, and an enlargement of this central hole to a larger diameter extending from its bottom to a point between the bottom and top; and a cylindrical elastic compliant and resilient member whose outer diameter is comparable to the diameter of the enlarged central hole in the upper part, and is inserted into it, such that when a crystal-holding tool is inserted into the upper part, the cylindrical elastic member grips the tool and holds it in place relative to the goniometer base.

Example 2

The goniometer base of example 1, where the cylindrical elastic member is made from rubber, synthetic rubber, neoprene rubber, silicone, or Teflon.

Example 3

The goniometer base of example 1, where the cylindrical elastic member has a central hole comparable in diameter to that of the crystal holding tool.

Example 4

The goniometer base of example 3, where the diameter of the central hole in the elastic member is 0.020".

Example 5

The goniometer base of example 3, where the diameter of the central hole is less than 0.025".

DEFINITIONS

Any and all published documents mentioned herein shall be considered to be incorporated by reference, in their respective entireties, herein to the fullest extent of the patent law. The following definitions are provided for claim construction purposes:

Present invention: means at least some embodiments of the present invention; references to various feature(s) of the "present invention" throughout this document do not mean that all claimed embodiments or methods include the referenced feature(s).

Embodiment: a machine, manufacture, system, method, process and/or composition that may (not must) meet the embodiment of a present, past or future patent claim based on this patent document; for example, an "embodiment" might not be covered by any claims filed with this patent document, but described as an "embodiment" to show the scope of the invention and indicate that it might (or might not) be covered in a later arising claim (for example, an amended claim, a continuation application claim, a divisional application claim, a reissue application claim, a re-examination proceeding claim, an interference count); also, an embodiment that is indeed covered by claims filed with this patent document might cease to be covered by claim amendments made during prosecution.

First, second, third, etc. ("ordinals"): Unless otherwise noted, ordinals only serve to distinguish or identify (e.g., various members of a group); the mere use of ordinals shall not be taken to necessarily imply order (for example, time order, space order).

Mechanically connected: Includes both direct mechanical connections, and indirect mechanical connections made through intermediate components; includes rigid mechanical connections as well as mechanical connection that allows for relative motion between the mechanically connected components; includes, but is not limited, to welded connections, solder connections, connections by fasteners (for example, nails, bolts, screws, nuts, hook-and-loop fasteners, knots, rivets, quick-release connections, latches and/or magnetic connections), force fit connections, friction fit connections, connections secured by engagement caused by gravitational forces, pivoting or rotatable connections, and/or slidable mechanical connections.

Standard X-ray crystallography operating conditions: immersion in cryogenic liquid, exposure to temperatures lower than 180 Kelvin and gas currents greater than 5 meters per second; it will be understood by those of skill in the art that this is not an industry standard, or a scientific standard, but rather a pragmatic standard for defining the forces and thermal affects that a typical rod/goniometer base engagement will be expected by practitioners to be capable of withstanding.

To the extent that the definitions provided above are consistent with ordinary, plain, and accustomed meanings (as generally shown by documents such as dictionaries and/or technical lexicons), the above definitions shall be considered supplemental in nature. To the extent that the definitions provided above are inconsistent with ordinary, plain, and accustomed meanings (as generally shown by documents such as dictionaries and/or technical lexicons), the above definitions shall control.

What is claimed is:

1. A goniometer-related assembly comprising:
a goniometer base housing structured, sized, shaped and/or having material properties to make it suitable for use in X-ray crystallography, with the goniometer base housing including a stage attachment hardware set structured, located, sized and/or shaped to be detachably attached to a goniometer stage assembly, wherein the goniometer base housing is shaped to define a first axis, a first axial direction and a first angular direction; and
a rod receiving hardware set that:
is mechanically connected to the goniometer base housing,
is sized, shaped, structured and/or located to releasably engage a sample-holding rod, and
is further sized, shaped, structured and/or located so that when the sample-holding rod is engaged by the receiving hardware set, the receiving hardware set will positionally secure the engaged sample-holding rod to some degree such that the engaged sample-holding rod: (i) is secured against movement by forces and thermal affects normally encountered under standard x-ray crystallography operating conditions, and (ii) is freely positionally adjustable by a user, relative to the goniometer base housing, in at least the first axial direction.

2. The assembly of claim 1 further comprising:
a goniometer stage assembly including:
a base attachment hardware set structured, located, sized and/or shaped to be detachably attached to the goniometer base housing through the stage attachment hardware set, and
positional adjustment hardware structured, located, sized and/or shaped to rotate the attached base housing about at least a second axis in a second angular direction.

3. The assembly of claim 2 wherein:
the stage attachment hardware set comprises magnetic material; and
the stage assembly further includes a magnetic goniometer head structured, sized, located and/or shaped to generate a magnetic field suitable to attach the goniometer base housing to the goniometer stage assembly through the magnetic securement of the stage attachment hardware set.

4. A goniometer-related assembly comprising:
a goniometer base housing; and
a deformable insert;
wherein:
the goniometer base housing structured, sized, shaped and/or having material properties to make it suitable for use in X-ray crystallography;
the goniometer base housing includes a stage attachment hardware set structured, located, sized and/or shaped to be detachably attached to a goniometer stage assembly;
the goniometer base housing defines a recess that defines an interior space, with the interior space being shaped to include an insert receiving sub-space and a rod receiving sub-space;
the goniometer base housing is shaped to define a first axis, a first axial direction and a first angular direction,
the deformable insert is located in the insert receiving sub-space;
the deformable insert is shaped, located, sized, structured and/or has material properties so that it will engage a rod when the rod is inserted into the rod receiving sub-space; and
the deformable insert is further shaped, located, sized, structured and/or has material properties so that when the rod is engaged by the receiving hardware set, the receiving hardware set will positionally secure the engaged sample-holding rod to some degree such that the engaged rod: (i) is secured against movement by forces and thermal affects normally encountered under standard x-ray crystallography operating conditions, and (ii) is freely positionally adjustable by a user, relative to the goniometer base housing, in at least the first axial direction.

5. The assembly of claim 4 wherein the deformable insert comprises substantially non-resilient deformable material.

6. The assembly of claim 4 wherein:
the deformable insert includes a resilient material portion; and
the resilient material portion defines a rod receiving recess shaped to engage with the rod with a resilient force fit.

7. The assembly of claim 4 wherein:
the goniometer base housing further includes an exterior surface;
the exterior surface is shaped to have cylindrical symmetry about the first axis; and
the interior space is shaped to have cylindrical symmetry about the first axis.

8. The assembly of claim 4 wherein:
the goniometer base housing is structured as a single, integral piece part;
the deformable insert includes a resilient material portion and a capping tube;
the resilient material portion defines a rod receiving recess shaped to engage with the rod with a resilient force fit;
the capping tube portion is rigidly mechanically connected to the goniometer base housing; and
the capping tube is located, structured, sized and/or shaped to prevent movement of the resilient material portion in the first axial direction.

9. The assembly of claim 8 wherein the resilient material portion is shaped as a cylindrical tube.

10. The assembly of claim 8 wherein:
the goniometer base housing further includes an exterior surface;
the exterior surface is shaped to have cylindrical symmetry about the first axis; and
the interior space is shaped to have cylindrical symmetry about the first axis.

11. The assembly of claim 4 wherein:
the deformable insert is shaped as a cylindrical tube;
the goniometer base housing comprises an upper piece and a lower piece;
the upper and lower pieces are structured, sized, shaped and/or located to be detachably attachable to each other;
the interior space is shaped as a cylindrical through hole including a first diameter portion and a second diameter portion;

the first diameter portion includes a portion of the rod receiving sub-space and has a first diameter that is: (i) sufficient to accommodate the rod, but (ii) insufficient to accommodate the deformable insert; and the second diameter portion includes the insert receiving sub-space, includes a portion of the rod receiving sub-space, and has a second diameter that is sufficient to accommodate the deformable insert.

12. The assembly of claim 11 wherein:
the goniometer base housing further includes an exterior surface;
the exterior surface is shaped to have cylindrical symmetry about the first axis; and
the interior space is shaped to have cylindrical symmetry about the first axis.

13. The assembly of claim 4 wherein the deformable insert is made entirely of resilient material.

14. The assembly of claim 13 wherein the deformable insert is made entirely of rubber.

15. An X-ray crystallography system comprising:
an X-ray source;
a cooling sub-system;
an X-ray sensor sub-system;
a goniometer stage assembly comprising a rotating portion;
a goniometer base housing;
a rod receiving hardware set; and
a sample-holding rod sub-system comprising a rod;
wherein:
the X-ray source is structured and/or located to supply X-ray radiation suitable for X-ray crystallography on a sample;
the cooling sub-system is structured and/or located to cool the sample down to a temperature suitable for X-ray crystallography;
the X-Ray sensor sub-system is structured and/or located to detect radiation from the X-ray source for X-ray crystallography purposes;
the sample-holding rod sub-system is sized, shaped, located and/or structured to hold the sample so that at least some of the X-ray radiation supplied by the X-ray source will be incident on the sample;
the rod defines a first axis, a first axial direction and a first angular direction;
the goniometer base housing is rigidly mechanically connected to the goniometer stage;
the rotating portion is rotatable in a second angular direction about at least a second axis so that the base member and rod receiving hardware are rotatable in the second angular direction by rotation of the rotating portion;
the rod receiving hardware set is mechanically connected to the goniometer base housing;
the rod receiving hardware set is sized, shaped, structured and/or located to releasably engage a portion of the rod, and
the rod receiving hardware set is further sized, shaped, structured and/or located so that when the rod is engaged by the receiving hardware set, the receiving hardware set will positionally secure the engaged rod to some degree such that the engaged rod: (i) is secured against movement by forces and thermal affects normally encountered under standard x-ray crystallography operating conditions, and (ii) is freely positionally adjustable by the user in at least the first axial direction.

16. The system of claim 15 wherein the first axis is at least substantially the same as the second axis.

17. The system of claim 15 wherein the first axis is not the same as the second axis.

18. The system of claim 15 wherein the cooling sub-system is structured and/or located to blow chilled gas on the sample.

19. The system of claim 15 wherein the cooling sub-system is structured and/or located to immerse the sample in chilled liquid.

20. The assembly of claim 15 wherein the rod receiving hardware set includes a cylindrical tube made of a resilient material.

21. A method comprising the steps of:
positively mechanically engaging a first rod, which is part of a first sample holding hardware set, with a first goniometer base, with the positive mechanical engagement between the first rod and the first goniometer base being sufficiently strong so that the first sample holding hardware, with its engaged first rod, will not move relative to the first goniometer base under standard X-ray crystallography operating conditions;
subsequent to the positively-mechanically-engaging-a-first-rod step, performing a first X-ray crystallography operation using the first goniometer base and the first sample holding hardware set with its engaged first rod;
subsequent to the performing-a-first-X-Ray-crystallography step, disengaging the first rod from the first goniometer base without damaging the first sample holding hardware set and without damaging the first goniometer base;
subsequent to the disengaging-the-first-sample-holding-hardware-set step, positively mechanically engaging a second rod, which is part of a second sample holding hardware set, with the first goniometer base, with the positive mechanical engagement between the second rod and the first goniometer base being sufficiently strong so that the second sample holding hardware, with its engaged second rod, will not move relative to the first goniometer base under standard X-ray crystallography operating conditions; and
subsequent to the positively-mechanically-engaging-a-second-rod step, performing a second X-ray crystallography operation using the first goniometer base and the second sample holding hardware set with its engaged second rod.

22. The method of claim 21 wherein:
during the positively-mechanically-engaging-a-first-rod step, a user inserts the first rod into a deformable insert and into the goniometer base so that the deformable insert engages the first rod with the goniometer base;
during the disengaging-the-first-sample-holding-hardware-set step, the user removes the first rod and the deformable insert from each other; and
during the positively-mechanically-engaging-a-second-rod step, the user inserts the second rod into the deformable insert and into the goniometer base so that the deformable insert engages the second rod with the goniometer base.

23. The method of claim 22 wherein the deformable insert is in the form of a cylindrical tube made of resilient material.

24. The method of claim 21 further comprising the steps of:
subsequent to the disengaging-the-first-sample-holding-hardware-set step, positively mechanically re-engaging the first rod with a second goniometer base, with the positive mechanical engagement between the first rod and the second goniometer base being sufficiently strong so that the first sample holding hardware, with its engaged first rod, will not move relative to the second goniometer base under standard X-ray crystallography operating conditions; and subsequent to the positively-mechanically-re-engaging step, performing a third X-ray crystallography operation using the second goniometer base and the first sample holding hardware set with its engaged first rod.

\* \* \* \* \*